(12) United States Patent
Takada

(10) Patent No.: US 9,423,236 B2
(45) Date of Patent: Aug. 23, 2016

(54) APPARATUS FOR OPTICAL INTERFEROMETRIC MEASUREMENT AND METHOD FOR THE SAME

(71) Applicant: Kabushiki Kaisha TOPCON, Tokyo (JP)

(72) Inventor: Akira Takada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 14/730,000

(22) Filed: Jun. 3, 2015

(65) Prior Publication Data
US 2015/0345931 A1    Dec. 3, 2015

(30) Foreign Application Priority Data

Jun. 3, 2014  (JP) ................. 2014-114884

(51) Int. Cl.
| G01B 9/02 | (2006.01) |
| G01N 21/85 | (2006.01) |
| A61B 5/026 | (2006.01) |
| A61B 5/00 | (2006.01) |

(52) U.S. Cl.
CPC .......... *G01B 9/02084* (2013.01); *A61B 5/0261* (2013.01); *A61B 5/7257* (2013.01); *G01B 9/02004* (2013.01); *G01B 9/0207* (2013.01); *G01N 21/85* (2013.01); *A61B 2560/0475* (2013.01); *A61B 2562/0233* (2013.01); *G01B 2290/60* (2013.01)

(58) Field of Classification Search
CPC ...... G01B 9/02; A61B 5/0066; A61B 5/6852; A61B 5/0073; G01N 21/4795
USPC ........................................ 356/479
See application file for complete search history.

(56) References Cited

U.S. PATENT DOCUMENTS

| 5,631,736 | A | 5/1997 | Thiel et al. | |
| 6,025,913 | A * | 2/2000 | Curbelo | G01J 3/447 250/339.08 |
| 2006/0132793 | A1* | 6/2006 | Ogawa | G01M 11/331 356/484 |

(Continued)

FOREIGN PATENT DOCUMENTS

WO    WO-2014/068323 A1    5/2014

OTHER PUBLICATIONS

European Search Report mailed Oct. 29, 2015, issued for the European patent application No. 15170234.7.

(Continued)

*Primary Examiner* — Tarifur Chowdhury
*Assistant Examiner* — MD M Rahman
(74) *Attorney, Agent, or Firm* — Locke Lord LLP

(57) ABSTRACT

An optical interferometric measurement apparatus includes an interference optical system to output a monitoring interference signal and a measurement interference signal in accordance with light emitted from a wavelength-swept light source, and a controller to measure a movement of an object to be measured. The controller has a storage to store monitoring data acquired by sampling the monitoring interference signal in each period of the light source and measurement data acquired by sampling the measurement interference signal in each period of the light source and Fourier transformation unit to apply Fourier transform to the measurement data. The controller determines a phase of the measurement interference signal based on the Fourier-transformed measurement data and measures the movement of the object based on the phase.

3 Claims, 7 Drawing Sheets

(56) References Cited

U.S. PATENT DOCUMENTS

| | | | |
|---|---|---|---|
| 2008/0165366 A1 | 7/2008 | Schmitt | |
| 2008/0266571 A1* | 10/2008 | Deck | G01H 1/06 356/450 |
| 2008/0291463 A1* | 11/2008 | Milner | A61B 1/00096 356/491 |
| 2009/0079993 A1* | 3/2009 | Yatagai | A61B 5/0062 356/497 |
| 2009/0103100 A1* | 4/2009 | Froggatt | G01M 11/3172 356/477 |
| 2009/0262359 A1* | 10/2009 | Bajraszewski | A61B 5/0066 356/454 |
| 2010/0149489 A1* | 6/2010 | Kikawa | A61B 3/102 351/206 |
| 2010/0149546 A1* | 6/2010 | Kobayashi | G01B 11/2441 356/511 |
| 2011/0261347 A1* | 10/2011 | Kassamakov | G01B 11/0675 356/51 |
| 2012/0105861 A1* | 5/2012 | Weitzel | A61B 5/0059 356/479 |
| 2012/0120408 A1* | 5/2012 | Yasuno | A61B 3/102 356/479 |

OTHER PUBLICATIONS

Braaf, et al "Phase-stabilized optical frequency domain imaging at 1-μm for the measurement of blood flow in the human choroid," Optics Express, vol. 19, No. 22, Oct. 24, 2011, pp. 20886-20903.

* cited by examiner

APPARATUS FOR OPTICAL INTERFEROMETRIC MEASUREMENT AND METHOD FOR THE SAME

CROSS-REFERENCE TO RELATED APPLICATION

The present application is based on and claims priority to Japanese patent application No. 2014-114884, filed Jun. 3, 2014, the disclosure of which is hereby incorporated by reference herein in its entirety.

BACKGROUND

1. Technical Field

This invention is related to an apparatus for optical interferometric measurement (optical interferometric measurement apparatus) and a method for the same. In particular, this invention is related to the apparatus and the method adapted to measure a movement of an object in shorter than or equal to the nanometer scale by acquiring a shift of a phase of an interference signal. The shift can be measured by using a point-spread-function that is determined by applying Fourier transform to the interference signal.

Conventionally, an optical interferometric measurement apparatus has been known. The conventional apparatus is configured to acquire measurement data by periodically sampling a spectrum interference signal, which is detected by an interferometer, and to determine a point-spread-function by applying Fourier transform to the acquired measurement data, thereby measuring a movement of an object based on a shift amount of a peak position in the determined point-spread-function.

This conventional optical interferometric measurement apparatus is, however, not able to detect (measure) a movement of the object in shorter than or equal to a micrometer scale since the point-spread-function itself spreads in the micrometer scale (i.e., the resolution of the point-spread-function is micrometer scale).

2. Description of Related Art

Here, an optical interferometric measurement apparatus that can measure a movement of an object in the sub-nanometer scale is taught by Non Patent Literature 1 (NPL 1): B. Braaf et al., "Phase-stabilized optical frequency domain imaging at 1-µm for the measurement of blood flow in the human choroid," Optics Express, USA, October 2011, Vol 19, No. 22, pp. 20886-20903. The apparatus of NPL1 is equipped with an optical interferometer for measurement (measuring interferometer) and an optical interferometer for reference (referring interferometer), acquires monitoring data by sampling a spectrum interference signal detected by the referring interferometer and measurement data by sampling a spectrum interference signal detected by the measuring interferometer, calculates correlation between the acquired monitoring data and the acquired measurement data, and removes a noise of the spectrum interference signal detected by the measuring interferometer, thereby achieving a measurement in the sub-nanometer scale.

SUMMARY

The apparatus of NPL 1 is configured to acquire monitoring data by sampling a spectrum interference signal detected by the referring interferometer, to acquire measurement data by sampling a spectrum interference signal detected by the measuring interferometer, and to calculate correlation between the monitoring data and the measurement data. Although this can achieve a measurement in the sub-nanometer scale, the calculation of the correlation takes a long time.

To solve the disadvantage, it is an object of the present invention to provide an apparatus and a method for optical interferometric measurement that can measure a movement in the sub-nanometer scale at a high processing speed.

To achieve the above object, an aspect of the present invention provides an optical interferometric measurement apparatus including an interference optical system adapted to output a monitoring interference signal and a measurement interference signal in accordance with light emitted from a wavelength-swept light source, and a controller adapted to measure a movement of an object to be measured. The controller includes a storage that stores monitoring data acquired by sampling the monitoring interference signal in each period of the light source and measurement data acquired by sampling the measurement interference signal in each period of the light source, a calculator that calculates a departure of a sweep start frequency from an average value of the sweep start frequencies in each period based on the monitoring data and converts the calculated departure into a difference in the number of sampling points, and a Fourier transformation unit that applies Fourier transform to the measurement data in each period. The calculator defines a maximum difference in the number of sampling points and aligns a sampling width of the measurement data in each period by removing data as many as the defined maximum difference in the number of sampling points from a sampling start point and retroactively from a sampling end point, The Fourier transformation unit applies the Fourier transform to the measurement data the width of which has been aligned by the calculator. Further, the controller determines a phase of the measurement interference signal based on the Fourier-transformed measurement data and measures the movement of the object based on the determined phase.

DETAILED DESCRIPTION

Hereinafter, an apparatus and a method for optical interferometric measurement according to an embodiment of the present invention will be explained with reference to the drawings.

Embodiment

Figure 1:
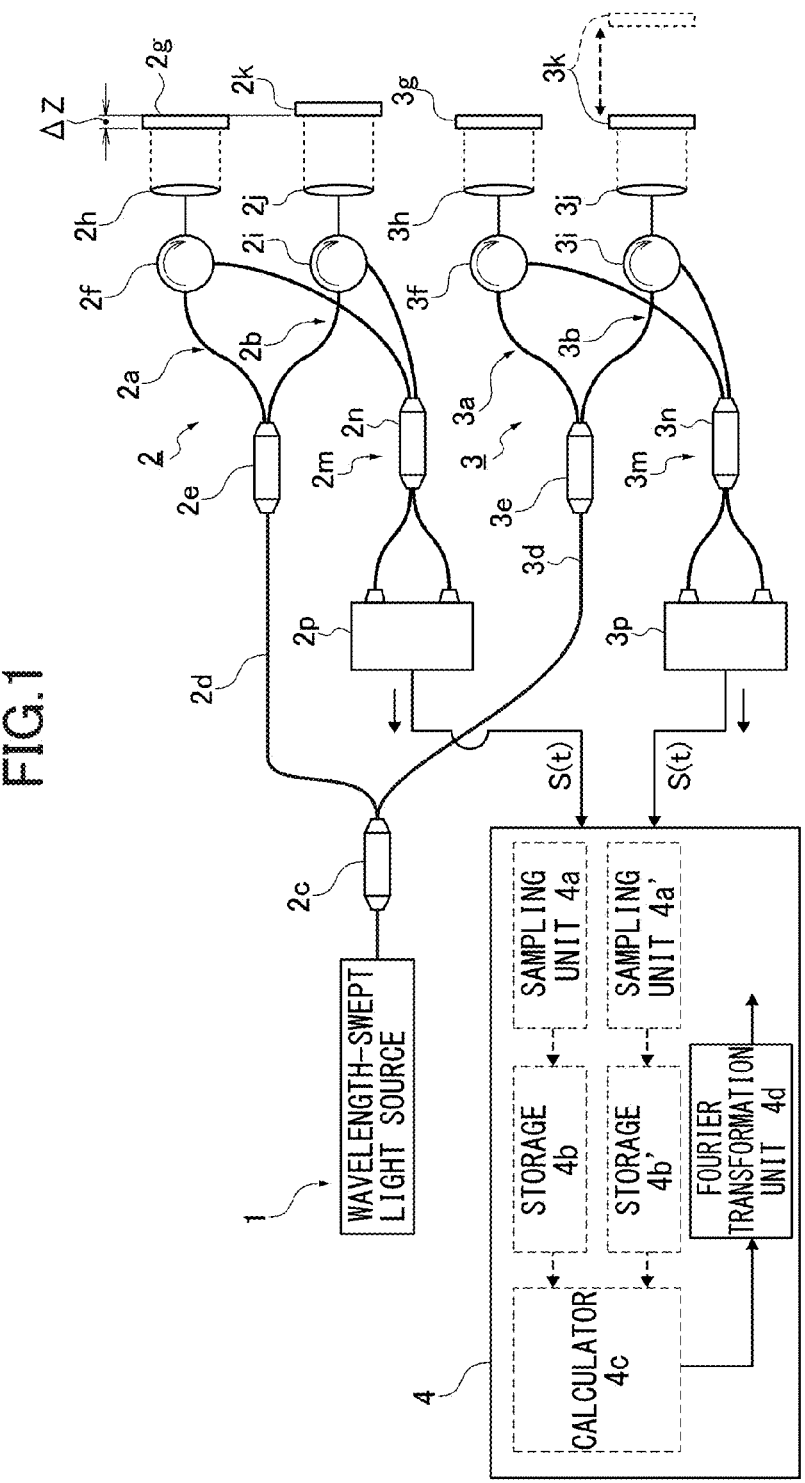
FIG. 1 is a schematic view for showing an example of an optical interferometric measurement apparatus according to an embodiment of the present invention.
Figure 2:
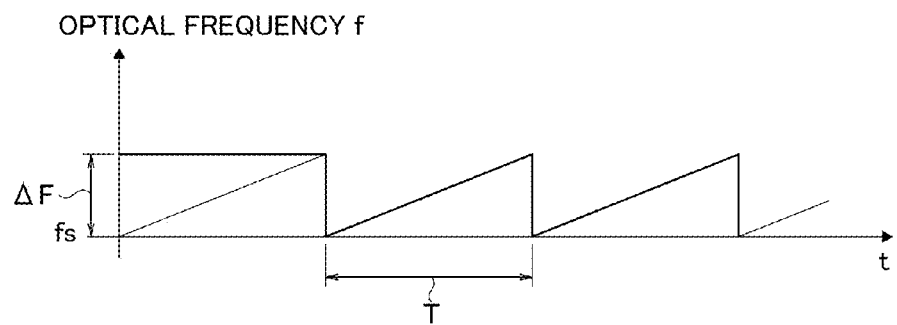
FIG. 2 is an explanatory view for schematically showing wavelength and a period of a wavelength-swept light source illustrated in FIG. 1.

FIG. 1 is a schematic overview showing an optical interferometric measurement apparatus according to an embodiment of the present invention. The optical interferometric measurement apparatus has a wavelength-swept light source 1. FIG. 2 is an explanatory view for showing an example of wavelength of the light source 1. Note a conventional wavelength-swept light source can be applied to the embodiment as the light source 1.

Figure 3:
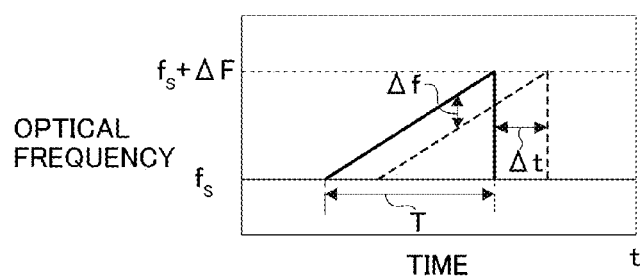
FIG. 3 is an explanatory view for showing a relation between a change of an optical frequency and an optical path difference.

Here, f represents an optical frequency, ΔF represents a frequency sweep width (wavelength sweep width), T represents a period (duration of a cycle) of the wavelength-swept light source 1, and fs represents a sweep start frequency (start frequency) of the light source 1 for each period T. Further, Δf shown in FIG. 3 represents a beat frequency generated in response to a difference in length (gap) between a reference optical path and a measurement optical path.

The optical interferometric measurement apparatus is equipped with a first interference optical system 2 as a monitoring interference optical system and a second interference optical system 3 as a measurement interference optical system. The first interference optical system 2 includes a first reference optical path 2a, a first measurement optical path 2b, and a combined optical path 2m. The light emitted from the wavelength-swept light source 1 is guided to both the first reference optical path 2a and the first measurement optical path 2b. Note in this specification, the first and second interference optical systems 2, 3 are collectively called an "interference optical system."

The first reference optical path 2a includes a photocoupler 2c, an optical fiber 2d, a photocoupler 2e, a circulator 2f, a collimator lens 2h, and a reference mirror 2g.

The first measurement optical path 2b includes the photocoupler 2c, the optical fiber 2d, the photocoupler 2e, a circulator 2i, a collimator lens 2j, and a measurement mirror 2k. The combined optical path 2m has a photocoupler 2n and a balanced detector 2p.

The light emitted from the wavelength-swept light source 1 is guided to the photocoupler 2c and divided into light guided to the first interference optical system 2 and light guided to the second interference optical system 3 by the photocoupler 2c. The light guided to the optical fiber 2d of the first interference optical system 2 is further divided by the photocoupler 2e and guided to the circulators 2f and 2i respectively.

The light guided to the circulator 2f is collimated into a parallel beam by the collimator lens 2h and guided to the reference mirror 2g. The parallel beam is then reflected by the reference mirror 2g and returned to the collimator lens 2h. The returned light is condensed by the collimator lens 2h and guided back to the circulator 2f.

The light guided to the circulator 2i is collimated into a parallel beam by the collimator lens 2j and guided to the measurement mirror 2k. The parallel beam is then reflected by the measurement mirror 2k and returned to the collimator lens 2j. The returned light is condensed by the collimator lens 2j and guided back to the circulator 2i.

The reference mirror 2g and measurement mirror 2k are fixed. A gap (difference in length) between the reference mirror 2g and measurement mirror 2k is represented as Δz and is expressed by: $\Delta z = z_2 - z_1$, where $z_1$ represents a total optical path length of the light passing through the first reference optical path 2a, and $z_2$ represents a total optical path length of the light passing through the first measurement optical path 2b.

The light reflected by the reference mirror 2g and guided back to the circulator 2f and the light reflected by the measurement mirror 2k and guided back to the circulator 2i are further guided to the photocoupler 2n on the combined optical path 2m. Both of the lights guided to the photocoupler 2n are then combined so as to interfere with each other and guided to the balanced detector 2p. The balanced detector 2p outputs a spectrum-monitoring interference signal (monitoring interference signal) S(t) in accordance with the lights guided thereto. The spectrum-monitoring interference signal S(t) includes the beat frequency Δf that is generated in response to the gap (difference in length) Δz.

The second interference optical system 3 includes a second reference optical path 3a, a second measurement optical path 3b, and a combined optical path 3m. The light emitted from the wavelength-swept light source 1 is guided to both the second reference optical path 3a and the second measurement optical path 3b.

The second reference optical path 3a includes the photocoupler 2c, an optical fiber 3d, a photocoupler 3e, a circulator 3f, a collimator lens 3h, and a reference mirror 3g.

The second measurement optical path 3b includes the photocoupler 2c, the optical fiber 3d, the photocoupler 3e, a circulator 3i, a collimator lens 3j, and an object to be measured 3k. The combined optical path 3m has a photocoupler 3n and a balanced detector 3p. Note although FIG. 3 schematically shows a mirror as the object 3k, this is only an example. The object 3k may be blood flow, for example.

The light emitted from the wavelength-swept light source 1 is divided by the photocoupler 2c. The light divided and guided to the optical fiber 3d of the second interference optical system 3 is further divided by the photocoupler 3e and then guided to the circulators 3f and 3i respectively.

The light guided to the circulator 3f is collimated into a parallel beam by the collimator lens 3h and guided to the reference mirror 3g. The parallel beam is then reflected by the reference mirror 3g and returned to the collimator lens 3h. The returned light is condensed by the collimator lens 3h and guided back to the circulator 3f.

The light guided to the circulator 3i is collimated into a parallel beam by the collimator lens 3j and guided to the object to be measured 3k. The parallel beam is then reflected by the object 3k and returned to the collimator lens 3j. The returned light is condensed by the collimator lens 3j and guided back to the circulator 3i.

The light reflected by the reference mirror 3g and guided back to the circulator 3f and the light reflected by the object 3k and guided back to the circulator 3i are further guided to the photocoupler 3n on the combined optical path 3m. Both of the lights guided to the photocoupler 3n are then combined so as to interfere with each other and guided to the balanced detector 3p.

The balanced detector 3p outputs a spectrum-measurement interference signal (measurement interference signal) S(t) in accordance with the lights guided thereto. The spectrum-measurement interference signal S(t) includes the beat frequency Δf that is generated in response to a gap (difference in length) between the reference mirror 3g and the object 3k. Note in this specification, the spectrum-measurement interference signal and the spectrum-monitoring interference signal are both expressed by the same reference character, S(t).

The spectrum-monitoring interference signal S(t) and the spectrum-measurement interference signal S(t) are inputted to a processor (controller) 4. The processor 4 includes sampling units 4a, 4a', storages (memories) 4b, 4b', a calculator 4c, and a Fourier Transformation unit 4d. The sampling unit 4a samples the spectrum-monitoring interference signal S(t) in each period T of the wavelength-swept light source 1. The sampled data is stored in the storage 4b as monitoring data.

The sampling unit 4a' samples the spectrum-measurement interference signal S(t) in each period T of the wavelength-swept light source 1. Note the sampling unit 4a' is synchronized with the sampling unit 4a to sample the spectrum-measurement interference signal S(t). The sampled data is stored in the storage 4b' as measurement data.

The monitoring data and the measurement data respectively stored in the storages 4b, 4b' are sent to the calculator 4c. The calculator 4c eliminates (removes) some data from the measurement data as described later. The remaining measurement data is sent to the Fourier transformation unit 4d and applied Fourier transform in each period T.

The Fourier transformation unit 4d determines a point-spread-function PSF(f) by multiplying the spectrum-measurement interference signal S(t) and a window-function W(t). To be specific, the point-spread-function PSF(f) is determined by the following equation:

$$PSF(f)=C\int S(t)W(t)\exp(i2\pi ft)dt \quad (1)$$

where C is a coefficient, and i represent an imaginary unit. Note the window-function W(t) is used to smooth the point-spread-function PSF(f).

As illustrated in FIG. 3, in the second interference optical system 3, time required for the light (reference light) to return from the reference mirror 3g and time required for the light (measurement light) to return from the object 3k differ from each other depending on the difference in the lengths of the optical paths. This time difference is expressed as a delay time $\Delta t$. Note a corresponding delay time $\Delta t$ in the first interference optical system 2 is a time difference between the time required for the light to return from the reference mirror 2g and time required for the light to return from the measurement mirror 2k.

Accordingly, the frequency of the measurement light increases by $\Delta f$ compared to the frequency of the reference light fs. Here, the frequency difference $\Delta f$ represents the beat frequency of the spectrum interference signal S(t).

The beat frequency $\Delta f$ corresponds to the variable f of the point-spread-function PSF(f). The variable f is expressed by:

$$f=\Delta F \cdot \Delta t/T \quad (2)$$

where $\Delta F$ represents the frequency sweep width. From the equation (2), the following equation is introduced:

$$c \cdot f \cdot T/\Delta F = c\Delta t \quad (3)$$

where c represents the speed of light.

Here, the gap $\Delta z$ (difference in length of the optical paths) is described as $c\Delta t$. Therefore, by determining the frequency sweep width $\Delta F$ and the variable f, it is possible to calculate the gap $\Delta z$. However, the accuracy of the gap $\Delta z$ calculated as explained above is limited to a scale of a half value width of the point-spread-function PSF(f). In other words, it is not possible to calculate the gap $\Delta z$ in less than or equal to the scale of the half value width of the point-spread-function PSF(f), particularly, it is limited to the micrometer scale.

To achieve a measurement in shorter than or equal to the nanometer scale, the embodiment uses phase data (phase) included in the point-spread-function PSF(f). However, the phase fluctuates. Hence, a low-pass filter having a cutoff frequency of 25 Hz is used to remove the temporal fluctuation of the phase.

Figure 4:
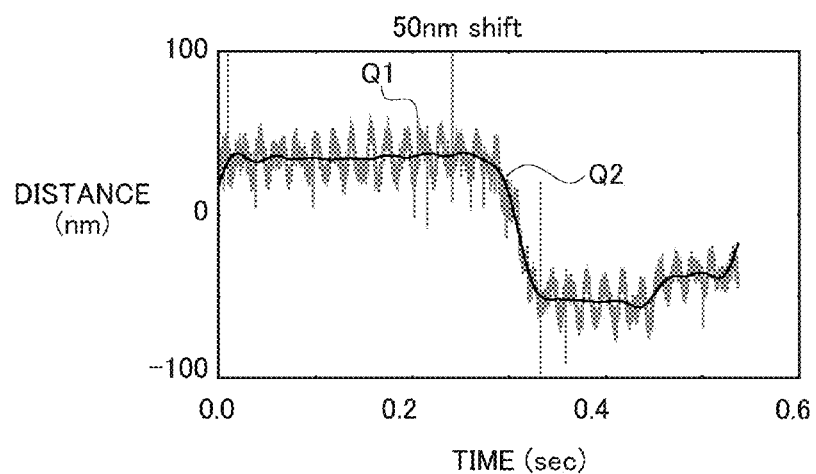
FIG. 4 is an explanatory view for showing raw data representing temporal change in distance, which corresponds to temporal fluctuation of a phase, detected when an object to be measured is intentionally moved, and for showing processed data acquired from the raw data by using a low-pass filter.

The optical interferometric measurement apparatus according to the embodiment determines the point-spread-function PSF(f) by applying Fourier transform to the spectrum-measurement interference signal S(t) acquired by using the reference mirror 3g and the object 3k in the second interference optical system 3. The apparatus then determines the phase $\phi$ from the point-spread-function PSF(f) and converts the temporal fluctuation of the determined phase $\phi$ into distances. FIG. 4 shows raw data of the distances. In this example, a movable minor is used as the object 3k.

In FIG. 4, the horizontal axis shows time, and the vertical axis shows movements (change of the distances) of the object 3k, which correspond to the temporal fluctuation of the phase $\phi$. The line Q1 represents the raw data of the change of the distances (i.e., the temporal fluctuation of the phase $\phi$), and the line Q2 represents processed data. The processed data is acquired by removing the temporal fluctuation of the phase $\phi$ with the low-pass filter and then by converting the data into distances.

Theoretically, the temporal fluctuation of the phase $\phi$ (phase error $\phi e$) does not appear unless the object 3k moves. However, the phase $\phi$ (raw data) determined based on the point-spread-function PSF(f) generally has temporal fluctuation as shown in FIG. 4. Using the low-pass filter removes the temporal fluctuation and gives a stable result of the phase $\phi$.

If the object 3k is intentionally moved (shifted), the phase $\phi$ shifts (fluctuates). Accordingly, it is possible to detect a movement (shift) of the object 3k based on the fluctuation of the phase $\phi$. The processed data Q2 of FIG. 4 shows the fluctuation of the phase $\phi$ when the object 3k is moved by 50 nm with respect to the reference minor 3g.

Figure 5:
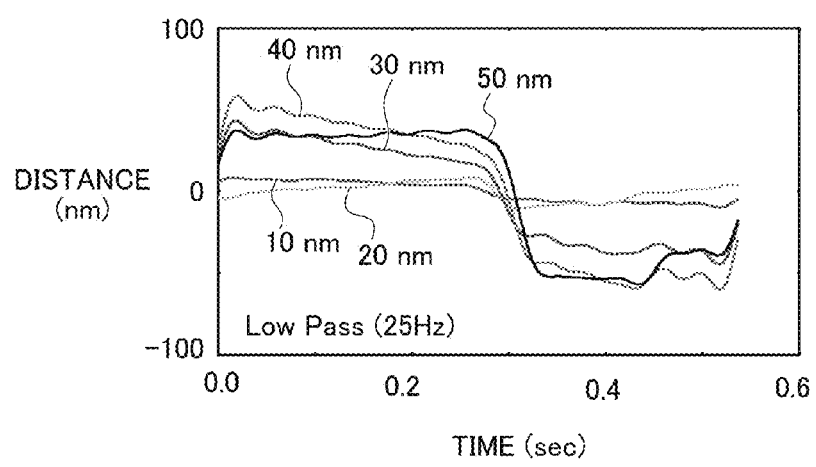
FIG. 5 is an explanatory view for showing several processed data acquired from corresponding raw data detected when the object is intentionally moved by 10 nanometers to 50 nanometers.

Further, FIG. 5 shows several processed data Q2 representing the fluctuations of the phase $\phi$ when the object 3k is moved by 10 nm, 20 nm, 30 nm, 40 nm, and 50 nm.

As clearly illustrated in FIGS. 4 and 5, it becomes possible to detect the movement of the object 3k in the nanometer scale by removing the temporal fluctuation of the phase $\phi$ (phase error $\phi e$). In the above explanation, the temporal fluctuations are removed by using the low-pass filter. However, the movement of the object 3k is unpredictable. For example, if the movement of the object 3k has the same period as the period of the temporal fluctuation of the phase, the low-pass filter may cutoff not only the fluctuation of the phase but also the fluctuation caused by the movement of the object 3k. As a result, removing the temporal fluctuation of the phase $\phi$ (phase error $\phi e$) by using the low-pass filter is not preferable and is unreliable.

To overcome such a deficiency, the inventors of the present invention considered about a relation between the phase error $\phi e$ and a difference in the number of sampling points (sampling shift).

When the gap (difference in length) $\Delta z$ between the reference minor 2g and the measurement mirror 2k of the first interference optical system 2 is set to be, for example, $\Delta z=5$ mm, the wavelength sweep width of the optical frequency of the wavelength-swept light source 1 is set to be, for example, 42 nm, the center wavelength of the wavelength-swept light source 1 is set to be, for example, $\lambda 0=1550$ nm (i.e., the optical frequency width is 5.2 terahertz (THz)), and the sweep time is set to be, for example, 20 $\mu s$ (i.e., the sweep frequency is 50 kHz); the beat frequency $\Delta f$ of the spectrum-monitoring interference signal S(t) is determined to be 9.0 MHz. Accordingly, when the signal S(t) does not have a phase error φe, the spectrum interference signal S(t) is drawn as the line (A) of FIG. 6.

Figure 6:
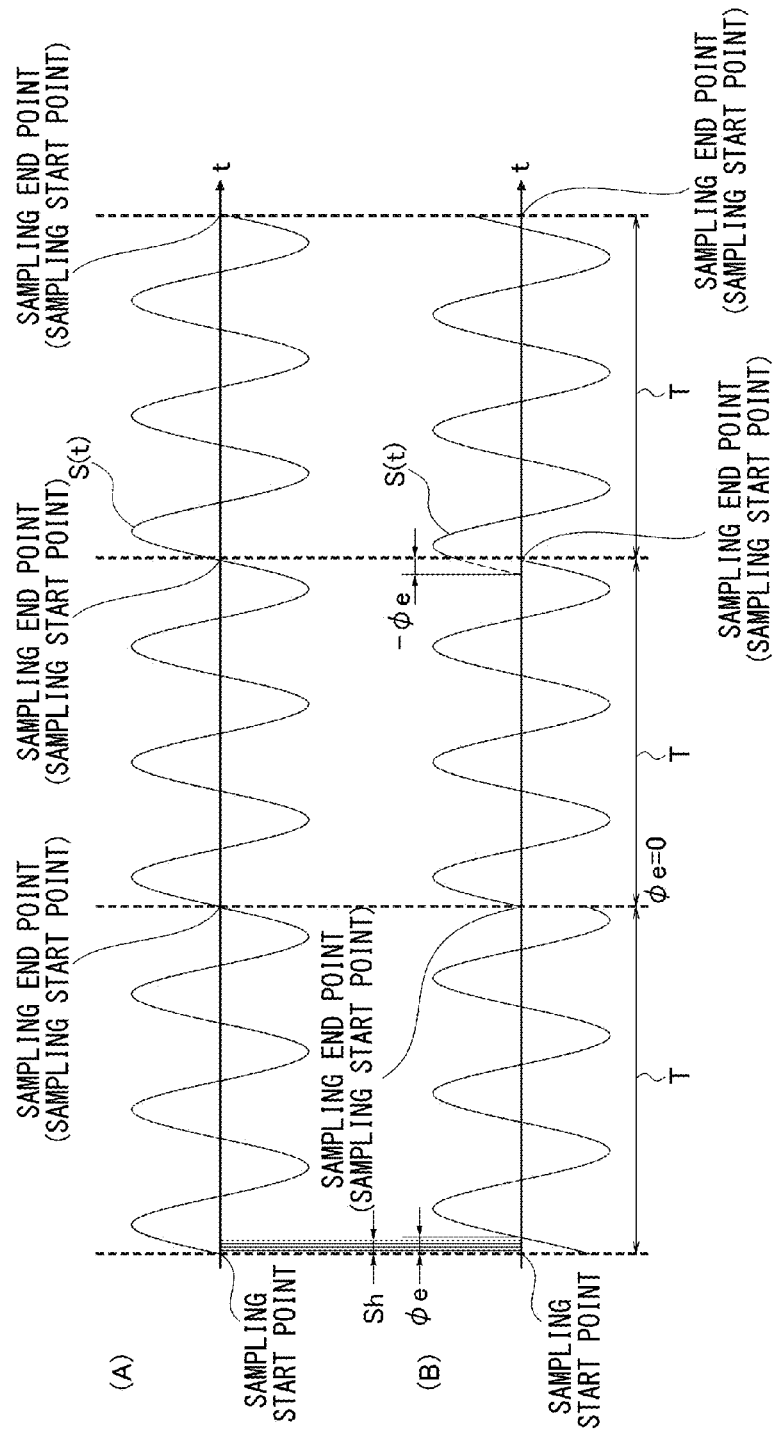
FIG. 6 is an explanatory view for showing a waveform of a spectrum interference signal without a phase error and a waveform of a spectrum interference signal having a phase error.

On the other hand, when the spectrum interference signal S(t) has a phase error φe in each period T, the signal S(t) is drawn as the line (B) of FIG. 6.

The phase error φe is expressed by:

$$\phi e = 2\pi \times sh \times \Delta f / Sf \quad (4)$$

where sh represents a departure from the sampling start point (i.e., the sampling shift, to be specific, difference in the number of sampling points), Δf represents the beat frequency of the spectrum interference signal, and Sf represents the sampling frequency (i.e., the number of sampling points per unit time S).

As a result, when the sampling frequency Sf is set to be, for example, 500 MHz, the beat frequency Δf is set to be, as explained above, 9 MHz, and the sampling shift is set to be 1; the phase error φe is determined to be φe=0.113 radian. By converting this phase error φe into a distance using the center wavelength (λ0=1550 nm), the gap Δz is determined to be Δz=14 nm. Since the sampling shift (difference in the number of sampling points) is normally 10 or more, the shift likely causes an inacceptable problem in the measurement in the nanometer scale. Note that the apparatus and the method of the embodiment uses a conventional equation to convert the phase error φe into a distance (length). This conventional equation is explained later.

As is known, intensities of optical interference fringes of the spectrum-monitoring interference signal S(t) can be expressed based on motion equations of optical vibrations on a complex plate. To be specific, the vibrations of the light passing through the first reference optical path 2a are expressed by: $\exp(i 2\pi f z_1/c)$, and the vibrations of the light passing through the first measurement optical path 2b are expressed by: $\exp(i 2\pi (f+\Delta f) z_2/c)$. Accordingly, the intensities of the optical interference fringes of the spectrum-monitoring interference signal S(t) are expressed by the square of the absolute value of: $\{\exp(i 2\pi f z_1/c) + \exp(i 2\pi (f+\Delta f) z_2/c)\}$.

By replacing $(2\pi f z_1/c)$ with α (i.e., $\alpha = 2\pi f z_1/c$) and $\{2\pi(f+\Delta f)z_2/c\}$ with β (i.e., $\beta = 2\pi(f+\Delta f)z_2/c$), the intensities of the optical interference fringes of the spectrum-monitoring interference signal S(t) are determined as follows:

$$\{\exp(i 2\pi f z_1/c) + \exp(i 2\pi (f+\Delta f) z_2/c)\} = \{\exp(i \cdot \alpha) + \exp(i \cdot \beta) = \quad (5)$$
$$(\cos\alpha + i\sin\alpha + \cos\beta + i\sin\beta) = \{(\cos\alpha + \cos\beta) + i(\sin\alpha + \sin\beta)\}$$

Since the intensities of the optical interference fringes are determined by the square of the absolute value of the above equation (5), they are determined by:

$$|\{(\cos\alpha + \cos\beta) + i(\sin\alpha + \sin\beta)\}|^2 = \quad (6)$$
$$\{\cos\alpha + \cos\beta + i(\sin\alpha + \sin\beta)\} \cdot \{\cos\alpha + \cos\beta - i(\sin\alpha + \sin\beta)\} =$$
$$(\cos\alpha + \cos\beta)^2 - i(\sin\alpha + \sin\beta) \cdot (\cos\alpha + \cos\beta) +$$
$$i(\sin\alpha + \sin\beta) \cdot (\cos\alpha + \cos\beta) - i^2(\sin\alpha + \sin\beta)^2 =$$
$$(\cos\alpha + \cos\beta)^2 + (\sin\alpha + \sin\beta)^2 = \cos^2\alpha + \cos^2\beta + 2\cos\alpha \cdot \cos\beta +$$
$$\sin^2\alpha + \sin^2\beta + 2\sin\alpha \cdot \sin\beta = 2 + 2\cos\alpha \cdot \cos\beta + 2\sin\alpha \cdot \sin\beta$$

Here, based on the formulas of trigonometrical function: $\cos(\alpha+\beta) = \cos\alpha \cdot \cos\beta - \sin\alpha \cdot \sin\beta$, $\cos(\alpha-\beta) = \cos\alpha \cdot \cos\beta + \sin\alpha \cdot \sin\beta$, the following equations are introduced:

$$\cos(\alpha+\beta) + \cos(\alpha-\beta) = 2 \cos\alpha \cdot \cos\beta$$

$$\cos(\alpha-\beta) - \cos(\alpha+\beta) = 2 \sin\alpha \cdot \sin\beta$$

Accordingly, the above equation (6) is expressed by:

$$2 + 2 \cos(\alpha - \beta). \quad (7)$$

In this equation, $\alpha = 2\pi f z_1/c$, $\beta = 2\pi(f+\Delta f)z_2/c$, and $\Delta z = z_2 - z_1$. Thus, $$\alpha - \beta =$$
$$(2\pi f z_1/c) - \{2\pi(f+\Delta f)z_2/c\} = \{2\pi f(z_2 - \Delta z)/c\} - \{2\pi(f+\Delta f)z_2/c\} =$$
$$(2\pi f z_2/c - 2\pi f \Delta z/c) - (2\pi f z_2/c + 2\pi \Delta f z_2/c) =$$
$$-(2\pi f \Delta z/c + 2\pi \Delta f z_2/c)$$

Consequently, the intensities of the optical interference fringes of the spectrum-monitoring interference signal S(t) are determined by:

$$2 + 2\cos(\alpha - \beta) = 2 + 2\cos\{-(2\pi f \Delta z/c + 2\pi \Delta f z_2/c)\} = \quad (8)$$
$$2 + 2\cos(2\pi f \Delta z/c + 2\pi \Delta f z_2/c)$$

That is to say, the spectrum-monitoring interference signal S(t) having the intensities of the optical interference fringes of: $4 \cos(2\pi f \Delta z/c + 2\pi \Delta f z_2/c)$, is outputted from the balanced detector 2p. Note the intensities of the optical interference fringes are doubled due to output characteristics of the balanced detector 2p. Further, the constant value "2" does not contribute to the measurement according to the embodiment of this present invention, and thus is neglected.

A difference in the sweep start frequency in each period T of the wavelength-swept light source 1 is considered to be the most influencing factor of the phase error φe. In the following, a relation between the difference in the sweep start frequency and the phase error φe is explained.

The sweep frequency f is expressed by:

$$f = fs + (\Delta F/T) t \quad (9)$$

where fs represents the sweep start frequency, ΔF represents the frequency sweep width, T represents the period of the light source 1, and t represents time.

As a result, the spectrum interference signal S(t) having the intensities of the optical interference fringes of: $4 \cos(2\pi f \Delta z/c + 2\pi \Delta f z_2/c)$ and being outputted from the balanced detector 2p, is expressed by:

$$4 \cos \{2\pi(fs+(\Delta F/T)t)\Delta z/c + 2\pi \Delta f z_2/c\} \quad (10)$$

When it is assumed that a shift (movement) of the sweep start frequency fs alone causes the phase error φe and that the sweep start frequency fs shifts by δfs in each period T, the term: $2\pi(fs+(\Delta F/T)t)\Delta z/c$ in the equation (10), is expressed by:

$$2\pi(fs+(\Delta F/T)t)\Delta z/c + 2\pi \delta fs \Delta z/c$$

Here, the term: $2\pi \delta fs \Delta z/c$, represents the phase error φe caused by the shift of the sweep start frequency fs. Therefore, the phase error φe is expressed by:

$$\phi e = 2\pi \delta fs \Delta z/c \quad (11)$$

Consequently, the phase error φe can be converted into the sampling shift sh based on the relation of the phase error φe, which is caused by the shift of the sweep start frequency fs, and the sampling shift (i.e., difference in the number of the sampling points) sh.

Figure 7:
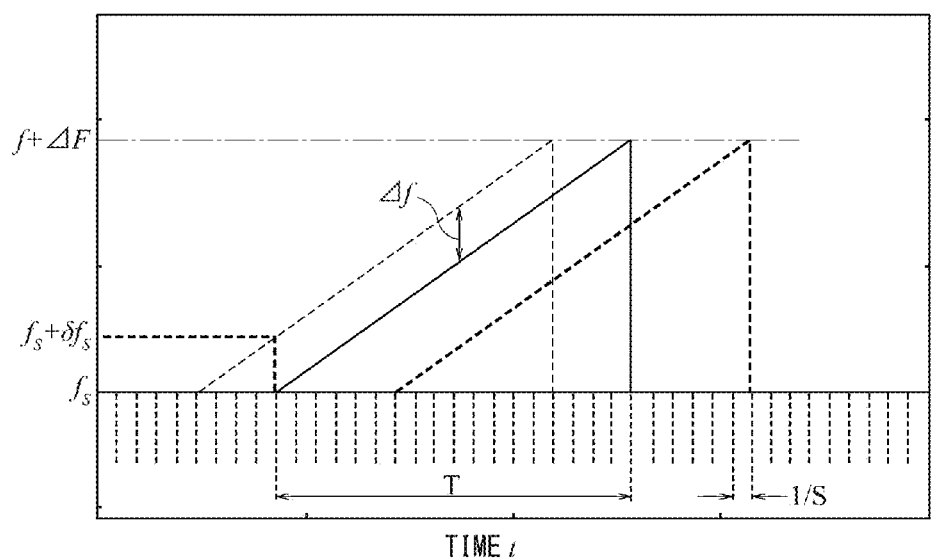
FIG. 7 is an explanatory view for explaining the phase error caused by a shift of sweep start frequencies.

FIG. 7 is an explanatory view for explaining the relation of the shift δfs of the sweep start frequency fs and the sampling shift sh (i.e., difference in the number of the sampling points).

When the sweep start frequency fs shifts from fs to fs+δfs, the relation of the sampling shift sh and the shift δfs of the sweep start frequency fs is expressed in accordance with the formula of the tangent as follows:

$$\delta fs / \{(1/S) \cdot sh\} = \Delta F/T$$

where S represents the number of the sampling points per unit time (1 second), and sh represents the difference in the number of sampling points (i.e., sampling shift) with respect to the original sweep start frequency (the average of the sweep start frequencies) fs.

As a result, the shift Δfs of the sweep start frequency fs is expressed by:

$$\delta fs = (\Delta F/T) \cdot \{(1/S) \cdot sh\} \quad (12)$$

By substituting the equation (12) into the equation (11), the phase error φe is expressed by:

$$\varphi e = 2\pi (\Delta F/T) \cdot \{(1/S) \cdot sh\} (\Delta z/c) \quad (13)$$

In the equation (3), the variable f corresponds to the beat frequency Δf. Hence, the equation (3) is expressed as: cΔf·T/ΔF=cΔt. Further, the gap Δz is expressed by Δz=cΔt. Accordingly, the equation (3) is re-expressed by: Δf=Δz·ΔF/(c·T) (i.e., ΔF=Δf·c·T/Δz). By substituting this equation into the equation (13), the phase error φe together with the sampling shift sh is expressed by:

$$\varphi e = 2\pi (\Delta f/S) \cdot sh \quad (14)$$

Monitoring data acquired by sampling the spectrum-monitoring interference signal S(t) is stored in the storage 4b and then inputted to the calculator 4c. The calculator 4c calculates the sampling shift (i.e., difference in the number of the sampling points) sh with respect to the average value of the sweep start frequencies fs in each period T. Specifically, the calculator 4c calculates the shift δfs of the sweep start frequency fs based on the monitoring data with respect to the average value of the sweep start frequency fs in each period T and calculates the difference in the number of sampling points in accordance with the shift δfs.

The calculator 4c further calculates the maximum sampling shifts (maximum difference in the number of sampling points) shm with respect to the average value of the sweep start frequencies fs in each period T.

The calculator 4c then aligns the sampling width H of the measurement data in each period T. To be specific, the calculator 4c respectively removes measurement data as many as the maximum sampling shift (maximum difference in the number of sampling points) shm from the sampling start point and retroactively from the sampling end point in each period T.

Figure 8:
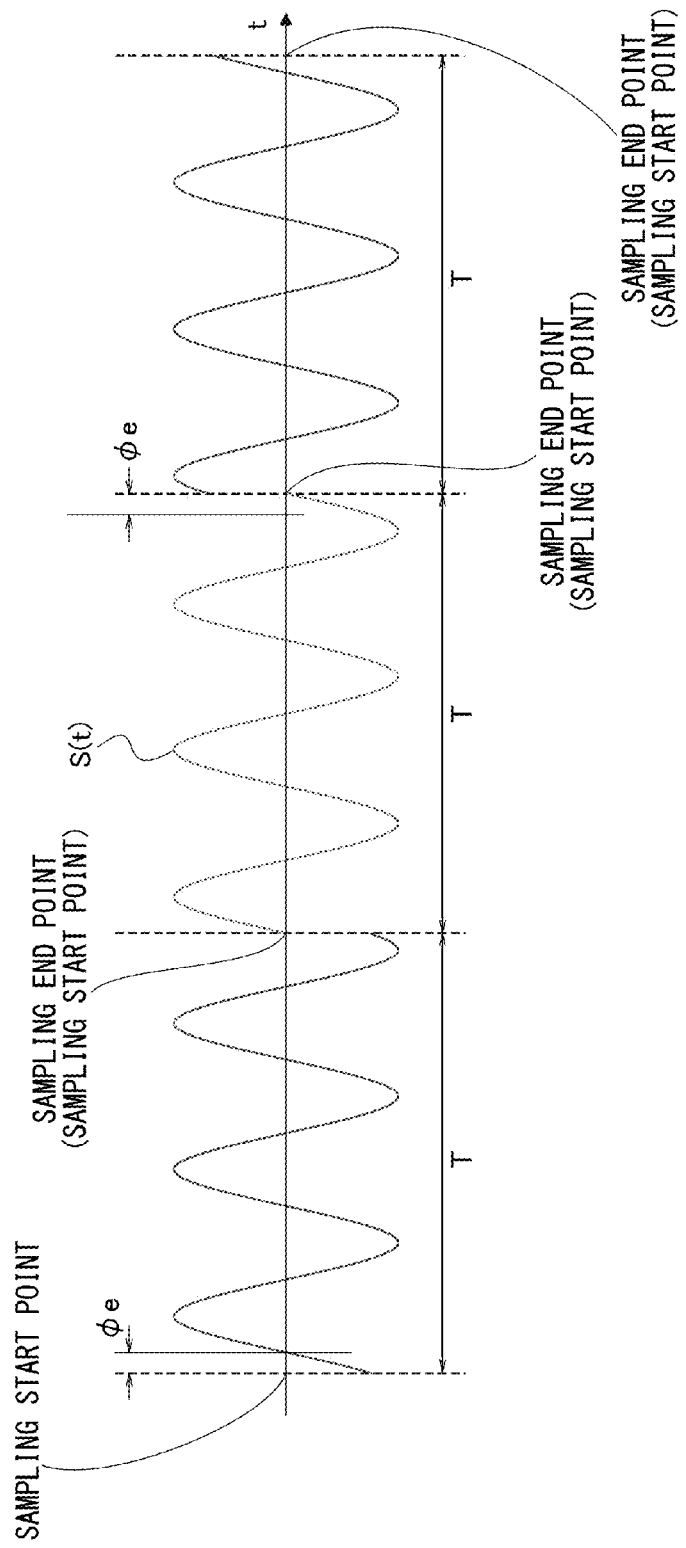
FIG. 8 is an explanatory view for showing a waveform of the spectrum-measurement interference signal having the phase error that is caused by the shift of sweep start frequencies.

FIG. 8 schematically shows the measurement data of the spectrum-measurement interference signal S(t) in each period T. In FIG. 8, the measurement data illustrated in the center does not have any phase error, the measurement data illustrated on the left side of the paper has the phase error +φe, and the measurement data illustrated on the right side of the paper has the phase error −φe.

Figure 9:
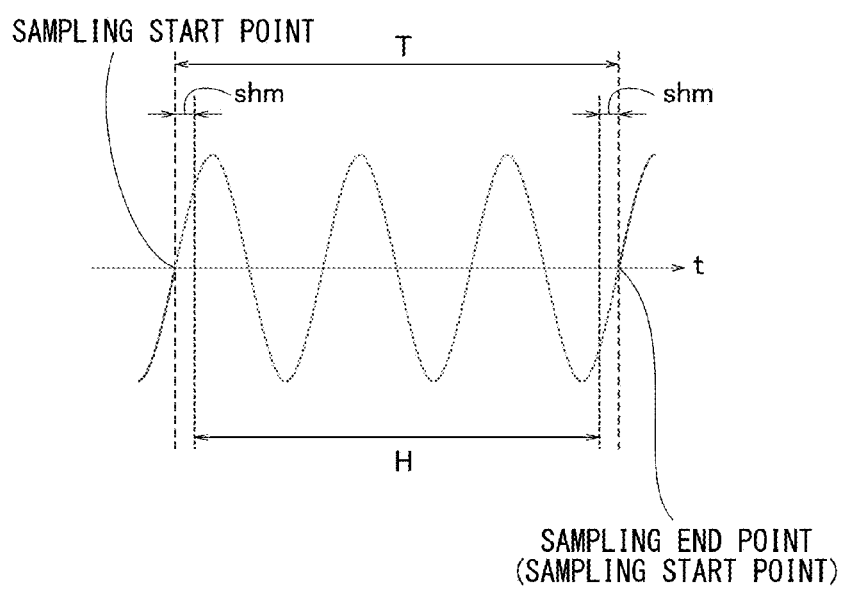
FIG. 9 is an explanatory view for showing the sampling data of FIG. 8 spectrum interference signal after aligning a sampling width of the sampling data.

As shown in FIG. 9, the calculator 4c aligns the sampling width H of the measurement data using the maximum sampling shift shm that is determined based on the monitoring data.

The measurement data is inputted to the Fourier transformation unit 4d in each period T after the sampling width H of the data is aligned. The Fourier transformation unit 4d applies the Fourier transform to the aligned measurement data in each period T and determines the point-spread-function PSF(f). As a result, the phase φ without the phase error φe is determined based on the point-spread-function PSF(f).

When the position of the object to be measured 3k is moved, the phase φ shifts from φ to φ'. The shift of the phase φ is expressed by: φ'−φ=2π·2Δz/λc, where λc represents the center wavelength of the sweep wavelength λ. Accordingly, the gap Δz can be determined in the nanometer scale or in the sub-nanometer scale by: Δz={(φ'−φ)/4π}×λc. Note that the equation to convert the phase difference (φ'−φ) into a distance (gap) is publicly known.

As explained above, the processor (controller) 4 of the embodiment stores the monitoring data, which is acquired by sampling the interference signal of the first interference optical system 2 in each period T, and the measurement data, which is acquired by sampling the interference signal of the second interference optical system 3 in each period T, into the storages 4b and 4b' (First Step).

The processor 4 then calculates the shift δfs of the sweep start frequency fs with respect to the average value of the sweep start frequency fs based on the monitoring data in each period T and calculates the difference in the number of sampling points (sampling shift sh) in accordance with the calculated shift δfs (Second Step).

The processor 4 further calculates the maximum sampling shifts (maximum difference in the number of sampling points) shm with respect to the average value of the sweep start frequencies fs in each period T (Third Step).

The processor 4 then aligns the sampling width H of the measurement data in each period T (Fourth Step). To be specific, the processor 4 respectively removes measurement data as many as the maximum sampling shifts (maximum difference in the number of sampling points) shm from the sampling start point and retroactively from the sampling end point in each period T.

The processor 4 further determines the distance (movement) based on the phase φ determined by applying Fourier transform in each period T to the measurement data acquired in Third Step. Consequently, the apparatus and the method according to the embodiment can detect a movement of the object to be measured 3k in the sub-nanometer scale based on the shift of the phase φ at a high processing speed (Fifth Step).

Further, when the optical interferometric measurement apparatus according to the embodiment is applied to an apparatus for blood flow speed measurement, it becomes possible to measure the blood flow rate by determining movements of, for example an erythrocyte (red blood-cell), as the object 3k per unit time.

Although the present invention has been described in terms of an exemplary embodiment, it is not limited thereto. It should be appreciated that variations or modifications may be made in the embodiment described by persons skilled in the art without departing from the scope of the present invention as defined by the following claims.

What is claimed is:

1. An optical interferometric measurement apparatus comprising:
   an interference optical system having a first set of a reference optical path and a measurement optical path with different total optical path lengths such that when separate light signals, emitted from a wavelength-swept light source, traveling along both optical paths are combined they interfere and create a monitoring interference signal and having a second set of a reference optical path and a measurement optical path with different total optical path lengths such that when separate light signals, emitted from the wavelength-swept light source, traveling along both optical paths are combined they interfere and create a measurement interference signal; and a processor for measuring a movement of an object to be measured, the processor stores monitoring data acquired by sampling the monitoring interference signal in each period of the light source and measurement data acquired by sampling the measurement interference signal in each period of the light source;

calculates a departure of a sweep start frequency from an average value of the sweep start frequencies in each period based on the monitoring data and converts the calculated departure into a difference in the number of sampling points; and applies Fourier transform to the measurement data in each period, wherein a maximum difference in the number of sampling points is defined and the processor aligns a sampling width of the measurement data in each period by removing data as many as the defined maximum difference in the number of sampling points from a sampling start point and retroactively from a sampling end point, wherein the Fourier transform is applied to the measurement data the width of which has been aligned, and wherein the processor determines a phase of the measurement interference signal based on the Fourier-transformed measurement data and measures the movement of the object based on the determined phase.

2. A method for optical interferometric measurement comprising:

providing an optical interferometric measurement apparatus of claim 1, a first step for storing monitoring data acquired by sampling a monitoring interference signal in each period of a wavelength-swept light source and measurement data acquired by sampling a measurement interference signal in each period of the light source;

a second step for calculating a departure of a sweep start frequency from an average value of the sweep start frequencies in each period based on the monitoring data and for converting the calculated departure into a difference in the number of sampling points;

a third step for defining a maximum difference in the number of sampling points;

a fourth step for aligning a sampling width of the measurement data in each period by removing data as many as the defined maximum difference in the number of sampling points from a sampling start point and retroactively from a sampling end point, and a fifth step for applying Fourier transform to the measurement data the width of which has been aligned in the fourth step in each period, for determining a phase of the measurement interference signal based on the Fourier-transformed measurement data, and for measuring the movement of an object to be measured based on the determined phase.

3. An apparatus for measuring blood flow rate comprising the optical interferometric apparatus according to claim 1.

* * * * *